(12) United States Patent
Slanda et al.

(10) Patent No.: US 11,090,040 B2
(45) Date of Patent: Aug. 17, 2021

(54) DELIVERY TOOLS FOR MEDICAL IMPLANTS AND METHODS OF USING THE SAME

(71) Applicant: Boston Scientific Scimed, Inc., Maple Grove, MN (US)

(72) Inventors: Jozef Slanda, Milford, MA (US); Peter J. Pereira, Mendon, MA (US); Manuel B. Teixeira, Boston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 233 days.

(21) Appl. No.: 15/387,185

(22) Filed: Dec. 21, 2016

(65) Prior Publication Data

US 2017/0181824 A1   Jun. 29, 2017

Related U.S. Application Data

(60) Provisional application No. 62/271,685, filed on Dec. 28, 2015.

(51) Int. Cl.
*A61B 18/08*   (2006.01)
*A61B 17/06*   (2006.01)
(Continued)

(52) U.S. Cl.
CPC ...... *A61B 17/0469* (2013.01); *A61B 17/0483* (2013.01); *A61B 17/06166* (2013.01);
(Continued)

(58) Field of Classification Search
CPC .. A61B 2017/0619; A61B 2017/00805; A61B 18/08; A61B 18/1442–1447
See application file for complete search history.

(56) References Cited

U.S. PATENT DOCUMENTS 4,662,068 A   5/1987 Polonsky et al.
5,565,122 A   10/1996 Wellington et al.
(Continued)

FOREIGN PATENT DOCUMENTS

EP   1321103 A2   6/2003

OTHER PUBLICATIONS

International Search Report and Written Opinion for PCT Application No. PCT/US2016/068263, dated Feb. 20, 2017, 15 pages.

*Primary Examiner* — Thaddeus B Cox
(74) *Attorney, Agent, or Firm* — Brake Hughes Bellerman LLP

(57) ABSTRACT

A medical device includes an energy delivery device. The energy delivery device has an elongate member, a first arm extending from the elongate member and a second arm extending from the elongate member. The first arm is configured to move with respect to the second arm. The energy delivery device includes an energy element. The energy element is configured to delivery energy to a portion of a filament when the filament is disposed between the first arm and the second arm. The energy device includes an actuation member. The actuation member is configured to move the first arm with respect to the second arm in response to the actuation member being actuated. The actuation member is operatively coupled to the energy element such that the energy element is activated in response to the actuation member being actuated.

20 Claims, 9 Drawing Sheets

(51) Int. Cl.
*A61B 17/04* (2006.01)
*A61B 18/04* (2006.01)
*A61B 17/00* (2006.01)

(52) U.S. Cl.
CPC ............ *A61B 18/04* (2013.01); *A61B 18/085* (2013.01); *A61B 2017/00734* (2013.01); *A61B 2017/00805* (2013.01); *A61B 2017/00951* (2013.01); *A61B 2017/0619* (2013.01)

(56) References Cited

U.S. PATENT DOCUMENTS

| | | | |
|---|---|---|---|
| 5,810,811 A * | 9/1998 | Yates | A61B 17/07207 |
| | | | 606/50 |
| 6,077,277 A * | 6/2000 | Mollenauer | A61B 17/04 |
| | | | 606/139 |
| 2002/0035371 A1 | 3/2002 | Westhaver et al. | |
| 2003/0114864 A1* | 6/2003 | McRury | A61B 17/0487 |
| | | | 606/148 |
| 2004/0073256 A1 | 4/2004 | Marchitto et al. | |
| 2004/0122451 A1* | 6/2004 | Wood | A61B 17/0057 |
| | | | 606/148 |
| 2006/0020167 A1 | 1/2006 | Sitzmann et al. | |
| 2006/0178680 A1* | 8/2006 | Nelson | A61B 17/0401 |
| | | | 606/139 |
| 2009/0234377 A1* | 9/2009 | Mahlin | A61B 17/0057 |
| | | | 606/153 |
| 2010/0016855 A1* | 1/2010 | Ramstein | A61B 1/00105 |
| | | | 606/49 |
| 2015/0265387 A1* | 9/2015 | Alexander | A61B 17/3468 |
| | | | 600/37 |

\* cited by examiner

DELIVERY TOOLS FOR MEDICAL IMPLANTS AND METHODS OF USING THE SAME

CROSS-REFERENCE TO RELATED APPLICATION

This application is a Nonprovisional of, and claims priority to, U.S. Patent Application No. 62/271,685, filed on Dec. 28, 2015, entitled "DELIVERY TOOLS FOR MEDICAL IMPLANTS AND METHODS OF USING THE SAME", which is incorporated by reference herein in its entirety.

TECHNICAL FIELD

The present invention generally relates to surgical devices and procedures, particularly devices and methods for the attachment of implants or tissues within a body of a patient.

BACKGROUND

Anatomical tissues such as pelvic tissues may be weakened or damaged with age, injury, or disease. This decrease in structural integrity of anatomical tissues may have significant medical consequences, which in turn might influence the biological functions of the tissues. There are various surgical procedures for treating such dysfunction of the tissues. Implants can be placed into a patient to provide support for the weakened or damaged tissue. The support provided by the implant may replicate the natural position and structure of the tissue, and thereby help in decreasing or eliminating impairment of biological functions resulting from tissue weakening or damage.

Some medical procedures, such as a laparoscopic sacrocolpopexy, may be performed on a patient to address the issues of weakened or damaged pelvic tissue. Some such procedures require coupling or fixing an implant to a tissue wall, such as a vaginal wall. In some cases, sutures are used to couple or fix the implant to the vaginal wall. This process may be time intensive as it may be difficult to tie knots in the suture to couple or fix the implant to the tissue and often times many knots are required to be tied (such as at various locations along the implant).

In view of the above, there is a need for improved delivery tools and improved methods of delivering or placing implants within a body of a patient.

SUMMARY

A medical device includes an energy delivery device. The energy delivery device has an elongate member, a first arm extending from the elongate member and a second arm extending from the elongate member. The first arm is configured to move with respect to the second arm. The energy delivery device includes an energy element. The energy element is configured to delivery energy to a portion of a filament when the filament is disposed between the first arm and the second arm. The energy device includes an actuation member. The actuation member is configured to move the first arm with respect to the second arm in response to the actuation member being actuated. The actuation member is operatively coupled to the energy element such that the energy element is activated in response to the actuation member being actuated.

In some embodiments, the energy delivery device is configured to deliver heat energy to the portion of the filament. In some embodiments, the actuation member is a single actuation member. In some embodiments, the filament is a suture.

In some embodiments, the actuation member is configured to simultaneously move the first arm with respect to the second arm and activate the energy element in response to the actuation member being actuated.

In some embodiments, the energy delivery device includes a handle portion, the handle portion extending from the elongate member. In some embodiments, the energy delivery device includes a handle portion, the handle portion extending from the elongate member, the handle portion having a portion that extends along an axis that is disposed at an angle with respect to a longitudinal axis of the elongate member.

In some embodiments, the energy device includes a first electrical contact and a second electrical contact, the first electrical contact being configured to contact the second electrical contact in response to the actuation member being actuated.

In some embodiments, the first arm is pivotally coupled to the elongate member. In some embodiments, the first arm is pivotally coupled to the elongate member, the second arm is pivotally coupled to the elongate member.

In some embodiments, the device includes an implant. In some embodiments, the implant is formed of a mesh material.

In some embodiments, the filament is configured to be coupled to a needle. In some embodiments, the elongate member includes a linear portion.

In some embodiments, a kit includes a filament having a first end portion and a second end portion, the first end portion of the filament being coupled to a needle; an energy delivery device, the energy delivery device having an elongate member, a first arm extending from the elongate member and a second arm extending from the elongate member, the first arm being configured to move with respect to the second arm, the energy delivery device including an energy element, the energy element being configured to delivery energy to a portion of a filament when the filament is disposed between the first arm and the second arm, the energy device including an actuation member, the actuation member being configured to move the first arm with respect to the second arm in response to the actuation member being actuated, the actuation member being operatively coupled to the energy element such that the energy element is activated in response to the actuation member being actuated; and an implant configured to be placed within a body of a patient.

In some embodiments, the energy delivery device is configured to deliver heat energy to the portion of the filament. In some embodiments, the filament is a suture. In some embodiments, the actuation member is configured to simultaneously move the first arm with respect to the second arm and activate the energy element in response to the actuation member being actuated.

In some embodiments, the energy delivery device includes a handle portion, the handle portion extending from the elongate member. In some embodiments, the energy delivery device includes a handle portion, the handle portion extending from the elongate member, the handle portion having a portion that extends along an axis that is disposed at an angle with respect to a longitudinal axis of the elongate member.

In another aspect a method of placing an implant within a body of a patient includes inserting the implant into the body of the patient such that the implant is disposed adjacent bodily tissue; passing a filament through the implant and through a portion of the bodily tissue; and actuating an actuation member of an energy delivery device to move a first arm of the energy delivery device with respect to a second arm of the energy delivery device and deliver energy a first portion of the filament to fuse the first portion of the filament to a second portion of the filament.

In some embodiments, the method includes inserting the energy delivery device into the body of the patient. In some embodiments, the method includes inserting the energy delivery device into the body of the patient such that first portion of the filament is disposed between a first arm of the energy delivery device and a second arm of the energy delivery device.

In some embodiments, the first arm is pivotally coupled to an elongate member of the energy delivery device. In some embodiments, the first arm is pivotally coupled to an elongate member of the energy delivery device, the second arm is pivotally coupled to the elongate member of the energy delivery device.

In some embodiments, the energy delivery device includes a handle portion extending from an elongate member.

BRIEF DESCRIPTION OF THE FIGURES

The invention and the following detailed description of certain embodiments thereof may be understood with reference to the following figures.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition).

The terms proximal and distal described in relation to various medical devices, apparatuses, and components as discussed in the subsequent text of the present invention are referred with a point of reference. The point of reference, as used in this description, is a perspective of an operator. The operator may be a surgeon, a physician, a nurse, a doctor, a technician, and the like, who may perform the procedure or surgery through the patient's body orifice or incision as described in the present invention. The term proximal refers to an area that is closer to the operator. The term distal refers to an area that is farther from the operator. The patient, as referred to here, can be a human female, male or any other mammal.

Although the present invention focuses on devices, systems and methods for use primarily for treatment of urinary incontinence or other type of pelvic floor disorder, the disclosed devices, systems and methods may be used to treat any type of medical condition or be used in any other procedure to place an implant within a body of a patient. In some embodiments, the processes according to embodiments of the invention couple the implant to bodily tissue in a shorter amount of time than using a suture to tie knots to couple an implant to bodily tissue. In some embodiments, the pull out force of the couplings is greater than 10 Newtons. In some embodiments, the procedures discussed below may be used via a laparoscopic device. As discussed below, in some embodiments, the devices may be used to couple the implant to bodily tissue at 10 or more or 12 or more locations.

Figure 1:
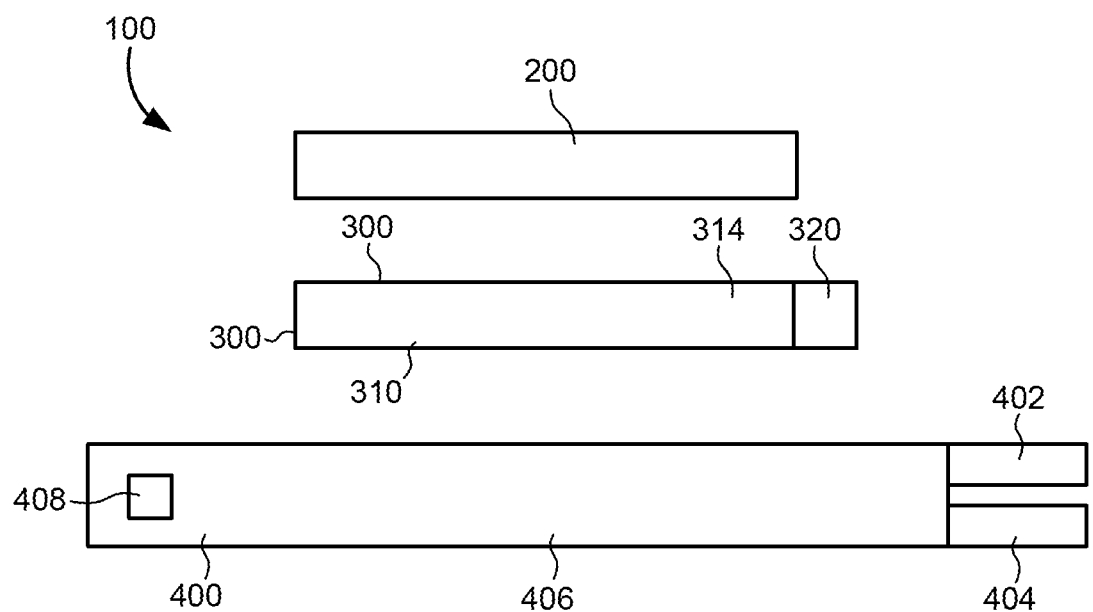
FIG. 1 is a schematic illustration of a medical device system according to an embodiment of the invention.

FIG. 1 is a schematic illustration of a medical system 100 according to an embodiment of the invention. The medical system 100 includes an implant 200, a filament system 300, and an energy delivery device 400. The items or devices of the medial system 100 may be packaged separately or may be packaged together as a kit. In some embodiments, only some of the items or devices are packaged together as a kit. For example, in some embodiments, only the filament system 300 and the energy delivery device 400 are packaged together as a kit. In other embodiments, other combinations of the items or devices are packaged together as a kit. In some embodiments, the kit may also include instructions for using the medical system 100.

The implant 200 may be placed within a body of a patient and coupled or fixed to bodily tissue within the body of the patient. For example, in some embodiments, the implant 200 may be inserted into the body of a patient and coupled to pelvic tissue or tissue within the pelvic region of the patient, such as a vaginal wall or tissue proximal to a vaginal wall of the patient. The implant 200 may be of any shape or size and may be formed of any type of biocompatible material. In some embodiments, the implant 200 is formed of a mesh material, such as a woven or knitted mesh.

The filament system 300 includes a filament 310 and a needle 320. In the illustrated embodiment, the filament 310 includes a first end portion 312 and a second end portion 314. The second end portion 314 is coupled to the needle 320. The needle 320 is configured to guide or lead the filament 310 through bodily tissue and through the implant 200.

The filament 310 is configured to extend through the implant 200 and though a portion of the bodily tissue of the patient. In some embodiments, a first portion the filament 310 is configured to extend through a second portion of the filament 310. In some embodiments, portions of the filament 310 may then be coupled to together to couple or fix the implant 200 to the bodily tissue.

In some embodiments, the filament 310 is formed of a material that is configured or formulated to accommodate the fusing of one portion of the filament 310 to another portion of the filament 310. For example, in some embodiments, the filament 310 may be formed of a material that is configured or formulated to have one portion of the filament 310 fuse to another portion of the filament 310 when energy, such as heat energy or radiofrequency (RF) energy or another type of energy, is applied to the portions of the filament 310. In some embodiments, the filament 310 is formed of or includes polyurethane. In other embodiments, the filament is formed of or includes polyvinylchloride (PVC). In yet other embodiments, the filament is formed of or includes one or more of the following materials: ABS polymers, acrylics, aclar, APET, Barex 210, Barex 218, butyrate, cellulose acetate (clear), cellulose acetate (color), cellulose acetate butyrate, cellulose nitrate, cellulose triacetate, ethylvinylacetate (EVA), ethylvinylalcohol (EVOH), melamine-formaldehyde resin, methylacrilate, nylon (polyamide), pelathane, polyethylene terphthate (PET), polyethylene terphthate glycol (PETG), polyamide, polymide, polymethyl (methacrylate), polystyrene, polyurethane, polyurethane-vinyl film, polyvinyl acetate, polyvinyl chloride (PVC) flexible-clear, and saran (polyvinylidene chloride). In some embodiment, the above materials are configured to facilitate the fusing of one portion of the filament 310 to another portion of the filament 310 when the portions of the filament are exposed to the energy (such as heat energy, RF energy, or another type of energy).

In some embodiments, the filament 310 may extend through the implant 200 and through a portion of the bodily tissue and the ends or portions of the filament 310 may be coupled or fused together to form a loop of filament thereby fixing or coupling the implant 200 to the bodily tissue. In some embodiments, the filament 310 may include a coating that is tacky or sticky (or is configured to stick to itself). In some embodiments, such adhesive coating may help hold the portions of the filament 310 together prior to the fusing of the portions. This holding of the portions of the filament 310 together may facilitate the process or step of fusing the portions of the filament 310 together.

The energy delivery device 400 is configured to deliver energy to portions of the filament 310. For example, once the filament 310 is passed through the implant 200 and the bodily tissue, the energy delivery device 400 may be used to delivery energy to ends or portions of the filament 310 to seal or fuse such portions of the filament 310 together. Accordingly, the filament 310 may form a complete loop of material to fix or couple the implant 200 to the bodily tissue. The energy delivery device 400 may be configured to delivery any type of energy to the portions of the filament 310. For example, in some embodiments, the energy delivery device 400 is configured to deliver heat energy to the portions of the filament 310. In other embodiments, the energy delivery device 400 is configured to deliver radiofrequency (RF) energy to the portions of the filament 310. In yet other embodiments, the energy delivery device 400 is configured to deliver another type of energy to the portions of the filament 310. In some embodiments, the energy delivery device 400 includes an elongate member (such as a body or shaft portion) 406 and arms or arm portions 402 and 404 that extend from the elongate member 406. In some embodiments, the energy delivery device 400 is configured to deliver energy to portions of the filament 310 that are disposed between the arms or arm portions 402 and 404. In some embodiments, the arm portions are configured to move. For example, in some embodiments, the arms are configured to be in an open or spaced position to allow the portions of the filament 310 to be placed between the arms. One or both arms may then be moved (towards each other) to a closed position. In some embodiments, placing the arms in the closed position helps facilitate the holding of one portion of the filament adjacent a second portion of the filament prior to the fusing of the portions of the filament.

For example, in some embodiments, the energy delivery device 400 may include an energy element such as coils, strips, or other members coupled to or integrated with the arm portions 402 and 404. The coils, strips or other members may be configured to receive and/or deliver the energy (such as heat energy, RF energy, or another type of energy) to the filament 310.

In some embodiments, the energy delivery device 400 includes an actuation member 408. The actuation member 408 is operatively coupled to the arms or arm portions 402 and 404 such that the arms or arm portions 402 and 404 are moved with respect to each other upon actuation of the actuation member 408. In some embodiments, the actuation of the actuation member 408 moves only one of the arms. In other embodiments, actuation of the actuation member moves both of the arms or arm portions 402 and 404. In some embodiments, the actuation member 408 is also operatively coupled to the energy element. In such embodiments, actuation of the actuation member activates the energy element such that energy may be delivered to portions of the filament 310. In some embodiments, actuation of the actuation member 408 simultaneously (or at the same or substantially the same time) moves the arm portions 402 and 404 with respect to each other and also activates the energy element. In some embodiments, a single actuation of the actuation member 408 moves the arm portions 402 and 404 with respect to each other and also activates the energy element. In some embodiments, the actuation member 408 is the only actuation member of the device. In other words, the device includes only one or a single actuation member.

Figure 2:
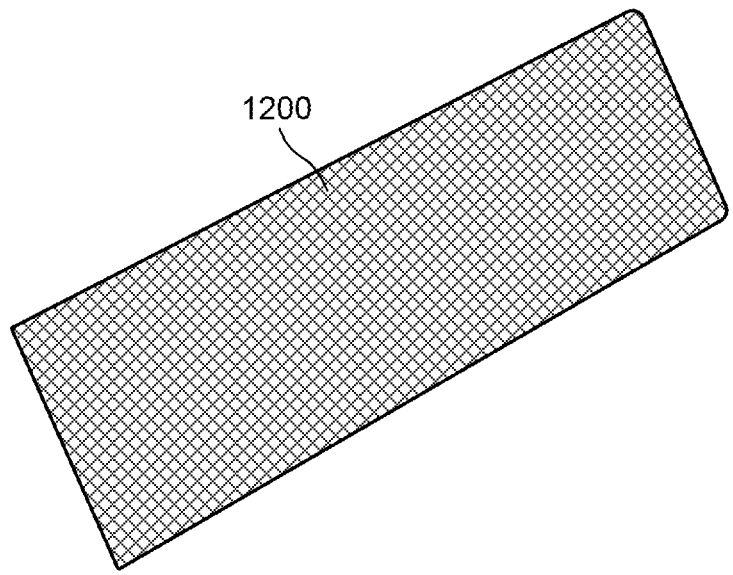
FIG. 2 is a perspective view of an implant according to an embodiment of the invention.

FIG. 2 is a perspective view of an implant 1200 according to an embodiment of the invention. The implant 1200 may be placed within a body of a patient and coupled or fixed to bodily tissue within the body of the patient. In some embodiments, the implant 1200 may be configured to help support or provide support to a portion of the body. For example, in some embodiments, the implant 1200 may be inserted into the body of a patient and coupled to pelvic tissue or tissue within the pelvic region of the patient, such as a vaginal wall or tissue proximal to a vaginal wall of the patient. Such an implant may be configured to provide support to a portion of the pelvic region of the patient, such as the bladder or the vagina of the patient.

The implant 1200 may be of any shape or size and may be formed of any type of biocompatible material. In the illustrated embodiment, the implant 1200 is rectangular and is formed as a mesh. In some embodiments, the mesh is a knitted mesh. In some embodiments, the mesh is Y-shaped.

Figure 3:
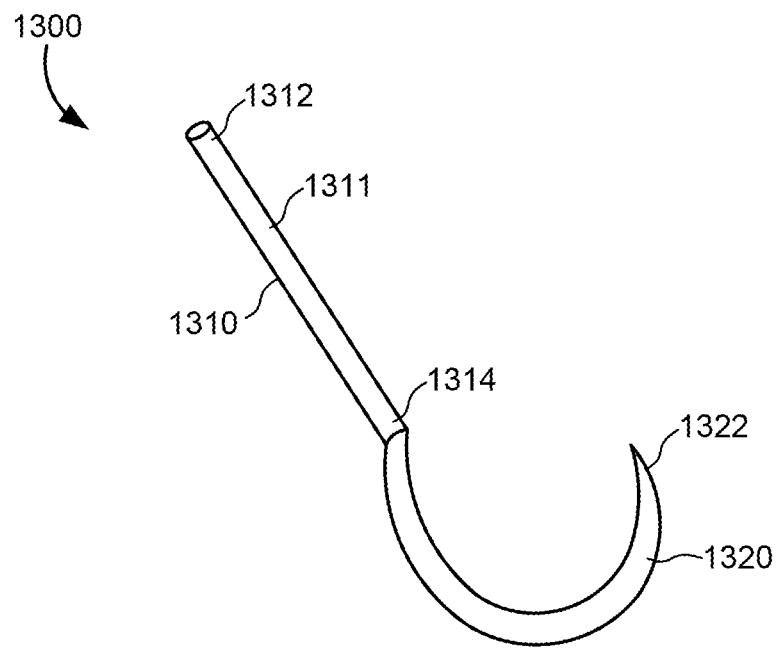
FIG. 3 is a perspective view of a filament coupled to a needle according to an embodiment of the invention.

FIG. 3 is a perspective view of a filament system 1300 according to an embodiment of the invention. The filament system 1300 includes a filament 1310 and a needle 1320. In the illustrated embodiment, the filament 1310 includes a first end portion 1312 and a second end portion 1314. The second end portion 1314 is coupled to the needle 1320. Any known method of coupling may be used to couple the second end portion 1314 to the needle 1320. For example, an adhesive, solder, or a swage joint may be used to couple the second end portion 1314 of the filament 1310 to the needle 1320.

The needle 1320 is configured to guide or lead the filament 1310 through through the implant 1200 and the bodily tissue. In the illustrated embodiment, the needle 1320 includes a tapered or sharp portion 1322 that is configured to pierce bodily tissue to help guide the filament through the bodily tissue. In the illustrated embodiment, the needle 1320 includes a curved portion. In other embodiments, the needle is linear or includes a linear portion.

The filament 1310 is configured to extend through the implant 1200 and though a portion of the bodily tissue of the patient. Portions of the filament 1310 may then be coupled to together to fix the implant 1200 to the bodily tissue. The filament 1310 may be of any shape or size. In the illustrated embodiment, the filament 1310 is a tubular member (has a circular or oval cross section). In some embodiments, the filament 1310 is a suture. In some embodiments, the filament 1310 has a flat and relatively rectangular cross section (such as a film).

In some embodiments, the filament 1310 is formed of a material that is configured or formulated to accommodate the fusing of one portion of the filament 1310 to another portion of the filament 1310. For example, in some embodiments, the filament 1310 may be formed of a material that is configured or formulated to have one portion of the filament 1310 fuse to another portion of the filament 1310 when energy, such as heat energy or radiofrequency (RF) energy or another type of energy, is applied to the portions of the filament 1310. In some embodiments, the filament 1310 is formed of or includes polyurethane. In other embodiments, the filament 1310 is formed of or includes polyvinylchloride (PVC). In yet other embodiments, the filament 1310 is formed of or includes one or more of the following materials: ABS polymers, acrylics, aclar, APET, Barex 210, Barex 218, butyrate, cellulose acetate (clear), cellulose acetate (color), cellulose acetate butyrate, cellulose nitrate, cellulose triacetate, ethylvinylacetate (EVA), ethylvinylalcohol (EVOH), melamine-formaldehyde resin, methylacrilate, nylon (polyamide), pelathane, polyethylene terphthate (PET), polyethylene terphthate glycol (PETG), polyamide, polymide, polymethyl (methacrylate), polystyrene, polyurethane, polyurethane-vinyl film, polyvinyl acetate, polyvinyl chloride (PVC) flexible-clear, and saran (polyvinylidene chloride). In some embodiment, the above materials are configured to facilitate the fusing of one portion of the filament 1310 to another portion of the filament 1310 when the portions of the filament are exposed to the energy (such as heat energy, RF energy, or another type of energy).

In some embodiments, the filament 1310 may extend through the implant 1200 and through a portion of the bodily tissue and back through the implant 1200 the ends or portions of the filament 1310 may be coupled or fused together to form a loop of filament thereby fixing or coupling the implant 1200 to the bodily tissue. In some embodiments, the filament 1310 may include a coating that is tacky or sticky (or is configured to stick to itself). For example, the filament 1310 may includes a coating on the outer surface 1311 of the filament 1310. In some embodiments, only a portion of the outer surface 1311 includes the coating. In some embodiments, such adhesive coating may help hold the portions of the filament 1310 together prior to the fusing of the portions. As will be described in more detail below, this holding of the portions of the filament 1310 together may facilitate the process or step of fusing the portions of the filament 1310 together.

Figure 4:
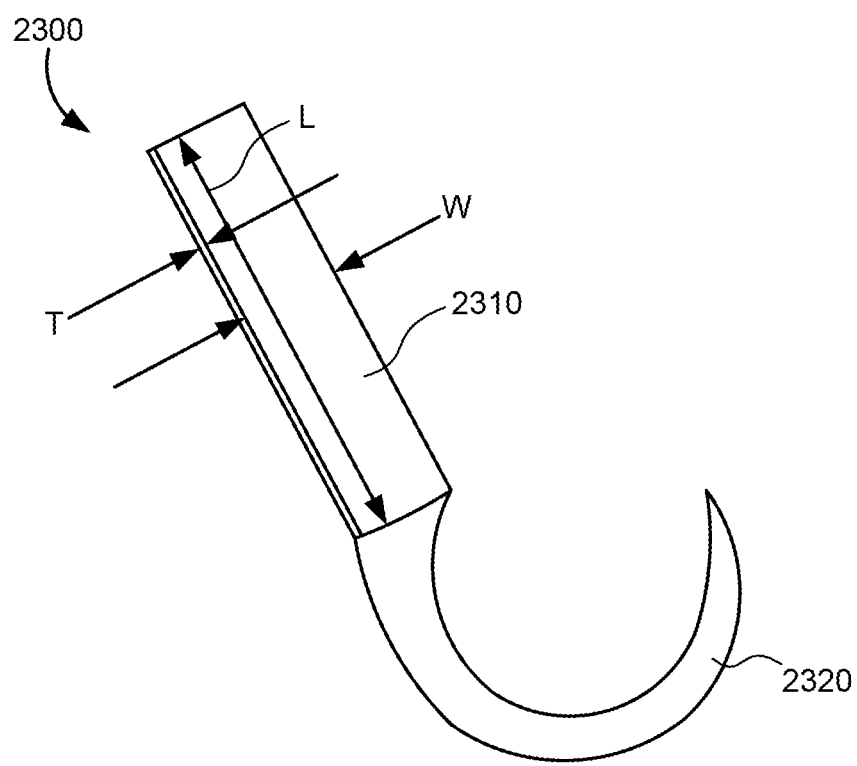
FIG. 4 is a perspective view of a filament coupled to a needle according to another embodiment of the invention.

FIG. 4 is a perspective view of a filament system 2300 in accordance with another embodiment of the invention. The filament system 2300 includes a filament 2310 that is coupled to a needle 2320. The filament 2310 is formed as a film or tape. In the illustrated embodiment the filament 2310 is a flat or planar film that has a length dimension L, a width dimension W, and a thickness dimension T. In the illustrated embodiment, the width dimension W is sufficient such that the filament 2310 or a portion of the filament 2310 may be passed through the filament along the width dimension W. In some embodiments, the length dimension L is greater than the width dimension W. Additionally, in some embodiments, the width dimension W is greater than the thickness dimension T. In some embodiments, the film or tape may be a solid member or may be a hollow member.

Figure 5:
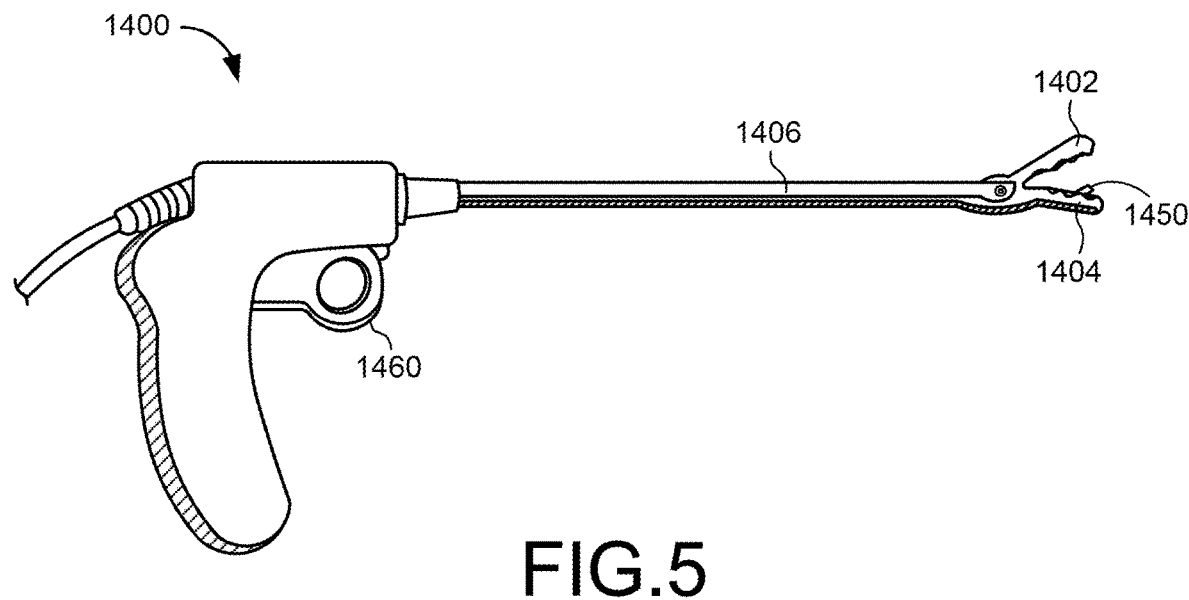
FIG. 5 is a side view of an energy delivery device according to an embodiment of the invention.
Figure 6:
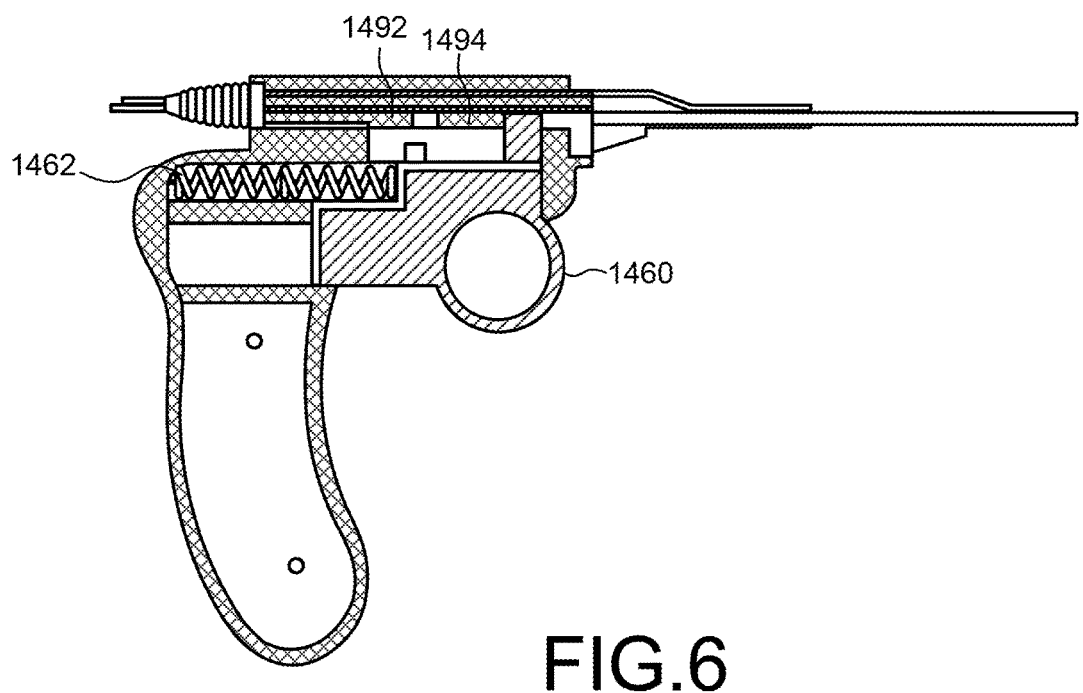
FIG. 6 is a cross-sectional side view of the energy delivery device of FIG. 5.

FIG. 5 is a perspective view of an energy delivery device 1400 in accordance with an embodiment of the invention. FIG. 6 is a side cross-sectional view of the energy delivery device 1400. The energy delivery device 1400 is configured to be disposed or placed within a body of a patient and to deliver energy to portions of the filament. For example, once the filament is passed through the implant, the bodily tissue and back through the implant, the energy delivery device 1400 may be used to delivery energy to ends or portions of the filament to seal or fuse such portions of the filament together. Accordingly, the filament may form a complete loop of material to fix or couple the implant to the bodily tissue. The energy delivery device 1400 may be configured to deliver any type of energy to the portions of the filament. For example, in some embodiments, the energy delivery device 1400 is configured to deliver heat energy to the portions of the filament. In other embodiments, the energy delivery device 1400 is configured to deliver radiofrequency (RF) energy to the portions of the filament. In yet other embodiments, the energy delivery device 1400 is configured to delivery another type of energy to the portions of the filament.

In the illustrated embodiment, the energy delivery device 1400 includes a elongate member (or a body or shaft portion) 1406 and arms or arm portions 1402 and 1404 that extend from the elongate member 1406. The energy delivery device 1400 is configured to deliver energy to portions of the filament that are disposed between the arms or arm portions 1402 and 1404. In the illustrated embodiment, only one of the arm portions 1402 and 1404 is configured to deliver energy to portions of the filament that are disposed between the arms or arm portions (and the other of the arm portions is configured to clamp or help retain the portions of the filament in place). In other embodiments, both of the arms or arm portions 1402 and 1404 are configured to deliver energy to portions of the filament that are disposed between the arms or arm portions.

In the illustrated embodiment, the arm portions are configured to move from a first or open position to a second or closed position. The arms are configured to be in the first (open or spaced) position to allow the portions of the filament to be placed between the arms 1402 and 1404. One or both arms may then be moved to the second or closed position. In some embodiments, placing the arms in the closed position helps facilitate the holding of one portion of the filament adjacent a second portion of the filament prior to the fusing of the portions of the filament. In the illustrated embodiment, arm portion 1402 is pivotally coupled to the elongate member 1406. Similarly, arm portion 1404 is pivotally coupled to the elongate member 1406. In other embodiments, another coupling method is used to couple the arm portions 1402 and 1404 to the elongate member 1406.

In the illustrated embodiment, the energy delivery device 1400 includes an energy element 1450. The energy element 1450 is configured to deliver the energy to the filament or the portion of the filament disposed between the arms 1402 and 1404. In some embodiments, the energy element 1450 is configured to contact the filament and deliver the energy to the portion of the filament that is being contacted. In the illustrated embodiment, the energy element 1450 is coupled to one of the arm portions. In other embodiments, the energy element is disposed at a different location on the energy delivery device 1400. In the illustrated embodiment, the energy delivery device 1400 includes only one or a single energy element. In other embodiments, the energy delivery device 1400 includes more than one energy element.

The energy delivery device 1400 includes an actuation member 1460. The actuation member 1460 is disposed at or near a proximal end portion of the energy delivery device 1400. In the illustrated embodiment, the actuation member 1460 is a trigger type actuation member. In other embodiments, the actuation member 1460 is of a different type or shape. In the illustrated embodiment, the actuation member 1460 is biased to a non-actuated state. A bias member, such as spring 1462, is disposed such that the actuation member 1460 is biased to a non-actuation state. The actuation member 1460 may be moved against the bias of the spring 1462 to place the actuation member in an actuated state. Releasing the actuation member 1460 will cause the actuation member 1460 to return to its non-actuated state or position.

Figure 7:
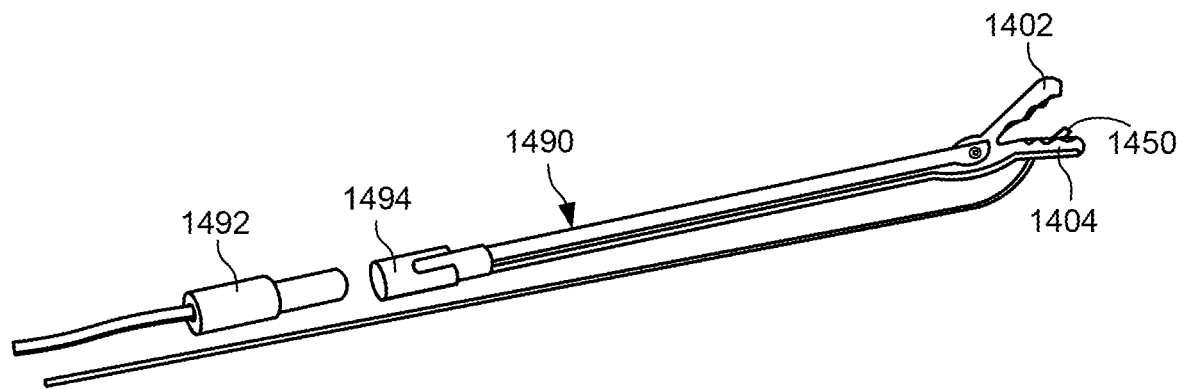
FIG. 7 illustrates the connections of the energy delivery device of FIG. 5.
Figure 8:
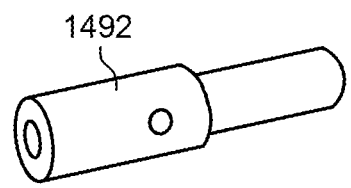
FIG. 8 is a perspective view of a contact of the energy delivery device of FIG. 5.
Figure 9:
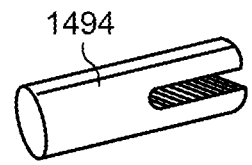
FIG. 9 is a perspective view of another contact of the energy delivery device of FIG. 5.

The actuation member 1460 is operatively coupled to the arms 1402 and 1404. Accordingly, when the actuation member 1460 is placed into its actuated state or position, the arms 1402 and 1404 move to their closed position. In other words, in response to the actuation member 1460 being placed into its actuated state or position, the arms 1402 and 1404 move with respect to each other (in a direction towards each other). As best illustrated in FIGS. 6 and 7, the actuation member 1460 is coupled to a linkage 1480 that is coupled to the arms 1402 and 1404. When the actuation member 1460 is moved to its actuated state or position, the arms 1402 and 1404 move towards each other (or from an open to a closed position).

The actuation member 1460 is also operatively coupled to the energy element 1450. When the actuation member 1460 is actuated or otherwise placed in its actuated position, the energy element 1450 is activated such that it may delivery energy to the filament or to a portion of the filament. As best illustrated in FIGS. 6-9, the energy delivery device 1400 includes an energy circuit 1490. In the illustrated embodiment, the circuit is an electrical circuit. The circuit 1490 includes a first contact 1492 and a second contact 1494. The contacts 1492 and 1494 are in a separated or spaced relationship when the actuation member 1460 is in its non-actuated state or position. When the actuation member 1460 is placed in its actuated state or position, the contacts 1492 and 1494 are place in contact with each other to complete or activate the electrical circuit 1490. The activation of the electrical circuit 1490 causes the energy element 1450 to heat up or deliver heat energy to the filament.

In one embodiment, the contacts 1492 and 1494 are formed of a electrically conductive material. In some embodiments, the contacts are formed of brass or partially formed of brass.

In the illustrated embodiment, movement of the actuation member 1460 to its actuated state or position (or actuation of the actuation member 1460) causes the arms 1402 and 1404 to move and the energy element 1450 to be activated at the same time (or simultaneously). In other words, a single actuation of the actuation member 1460 causes the arms 1402 and 1404 to move and the energy element 1450 to be activated. In other embodiments, the actuation member 1460 causes the arms 1402 and 1404 to move and the energy element 1450 to be activated at different times.

In the illustrated embodiment the device 1400 includes one and only one (or a single) actuation member 1460. Accordingly, the physician or medical practitioner may easily use the device 1400 to fuse ends of the filament. In other embodiments, the device may include more than one actuation member.

Figure 10:
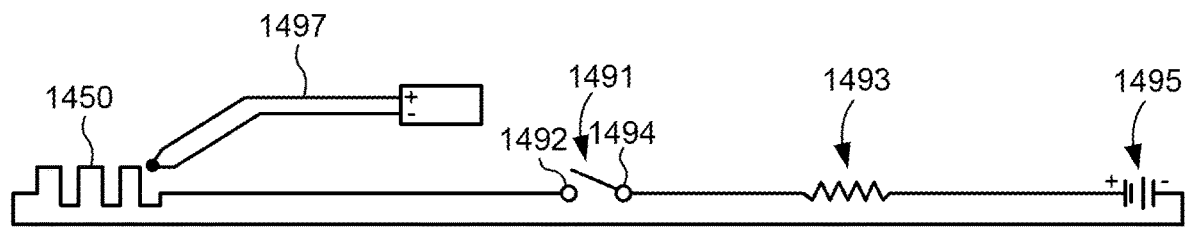
FIG. 10 is a wiring diagram of the energy delivery device of FIG. 5.

FIG. 10 is a wiring diagram for the electrical circuit 1490. The switch 1491 is formed by the contacts 1492 and 1494. The electrical circuit 1490 includes a resistor 1493, a battery or source 1495, the energy element 1450, a thermocouple 1497 and a thermometer 1499. The components are operatively coupled together via wire, such as 16 gauge wire. In the illustrated embodiment, the battery or source 1495 is coupled to the device 1400 via an electric cable 1489 that extends from the proximal end portion of the device 1400. In some embodiments, the battery or source is a 3 volt or 6 volt battery. In other embodiments, the battery or source is of a different voltage.

In the illustrated embodiment, a portion of the electrical circuit 1490 is disposed within the elongate member 1406 (such as within a lumen defined by the elongate member 1406) and a portion is disposed outside of the elongate member 1406. In other embodiments, the electrical circuit 1490 is entirely disposed within the elongate member 1406.

Figure 12:
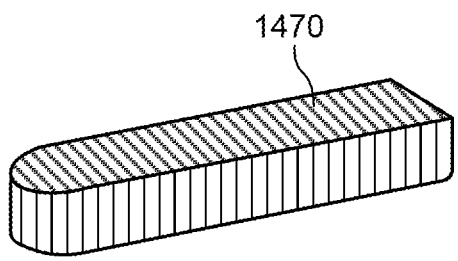
FIG. 12 is a perspective view of a pad of the energy device of FIG. 5.

FIG. 12 illustrates a pad 1470 that is disposed on arm 1402. The pad 1470 is coupled to the arm 1402. In some embodiments, the pad 1470 is glued to the arm 1402. In some embodiments, the pad 1470 includes a teflon cover. In some embodiments, the pad 1470 is configured to help grip or retain the filament.

Figure 11:
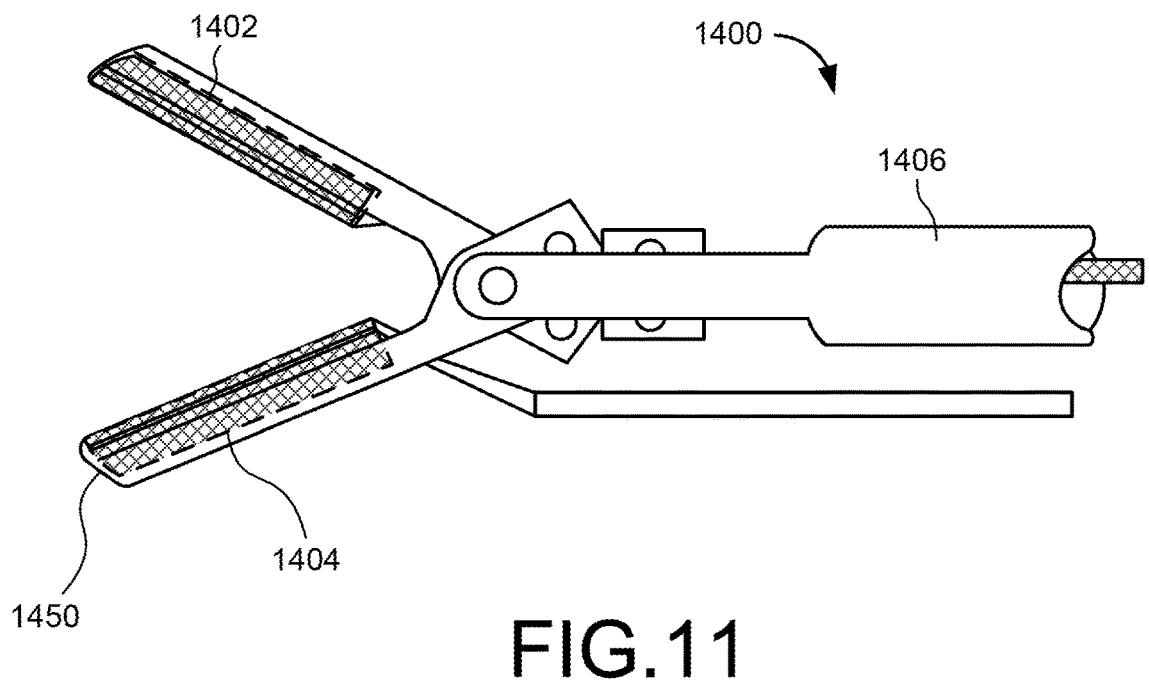
FIG. 11 is a side view of an end portion of the energy delivery device of FIG. 5.
Figure 13:
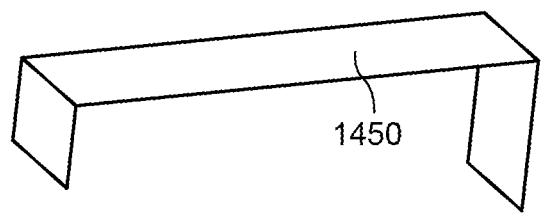
FIG. 13 is a perspective view of an energy element of the energy device of FIG. 5.
Figure 14:
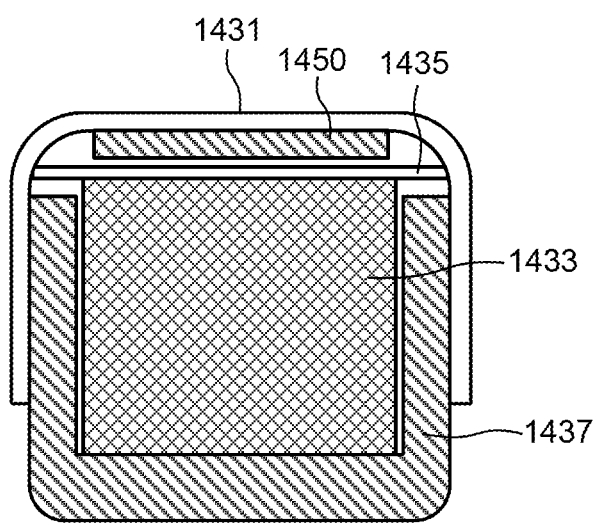
FIG. 14 is a top view of an arm of the energy device of FIG. 5.

FIG. 13 illustrates the energy element 1450. As illustrated in FIG. 11, the energy element 1450 is coupled to the arm 1404. FIG. 14 is a cross-sectional view of arm 1404. In the illustrated embodiment, a teflon cover 1431 is disposed over the energy element 1450. The energy element 1450 is coupled to a pad 1433 via teflon tape 1435. The pad 1433 is disposed within a slot 1437 defined by the arm portion 1404.

The energy delivery device 1400 includes a handle 1420. The handle 1420 includes a grip portion or a portion that is configured to be gripped or grasped by a user or medical practitioner. The handle 1420 includes a curved portion. In the illustrated embodiment, the handle 1420 includes a portion 1421 that has a axis AX that is offset or disposed at an angle with respect to a longitudinal axis LA of the elongate member 1406.

Figure 15:
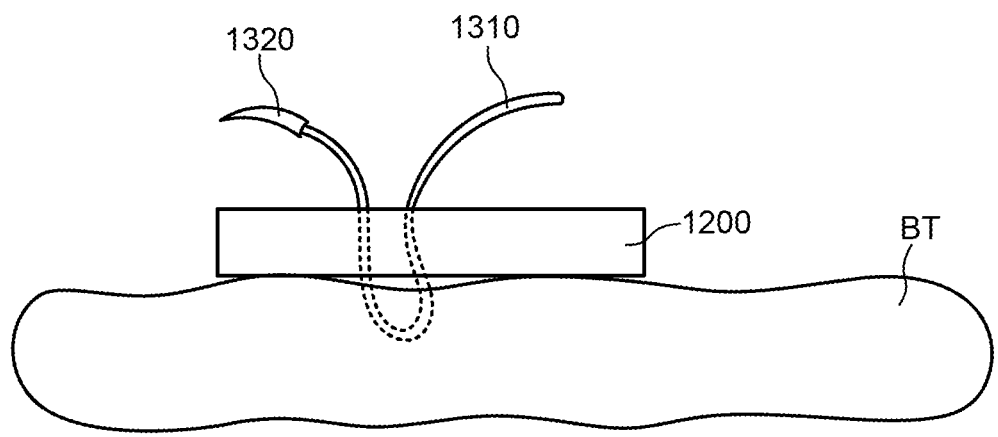
FIG. 15-18 schematically a bodily implant being place within a body of a patient.

FIGS. 15-18 schematically illustrate a process of fixing or coupling an implant within a body of a patient according to an embodiment of the invention. As illustrated in FIG. 15, the implant 1200 may be placed within a body of a patient and disposed adjacent to bodily tissue BT. The filament 1310 may then be passed through the implant 1200, through the bodily tissue BT, and back through the implant 1200. In some embodiments, the filament 1310 does not extend entirely through the bodily tissue BT. For example, if the implant 1200 is being coupled or fixed to an outer surface of a vaginal wall of a patient, the filament need not pass entirely through the vaginal wall. In some cases, the filament will only be passed through a portion of the thickness of the vaginal wall.

Figure 16:
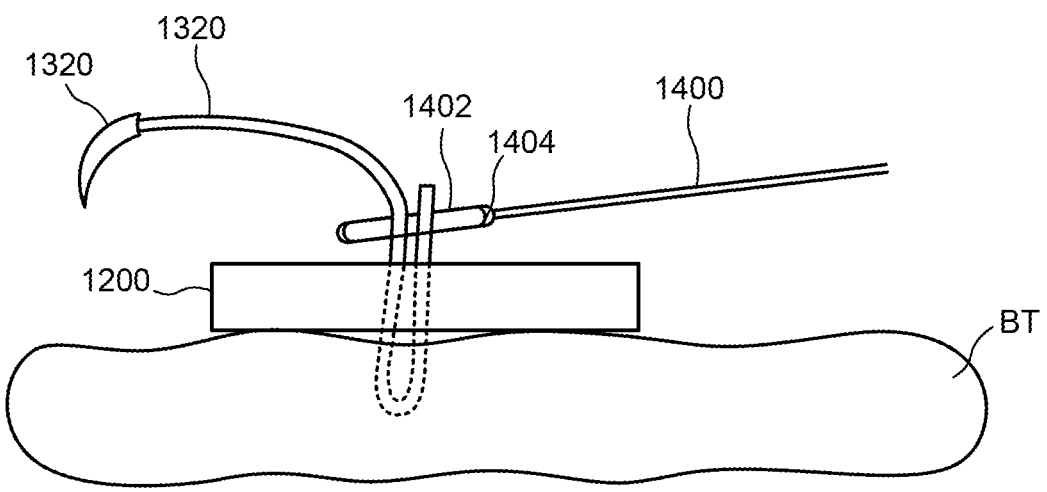

As illustrated in FIG. 16, portions of the filament 1310 may be disposed between the arms 1402 and 1404 of the energy delivery device 1400. The arms 1402 and 1404 may be moved to their closed positions to approximate the portions of the filament that are disposed between the arms. In some embodiments, when the arms 1402 and 1404 are disposed in their second or closed positions, the portions of the filament that are disposed between the arms are in contact with one another. The delivery device 1400 may then deliver energy to the portions of the filament 1310 that are disposed between the arms 1402 and 1404. The portions of the filament that receive the energy are configured to fuse together upon receiving the energy.

Figure 17:
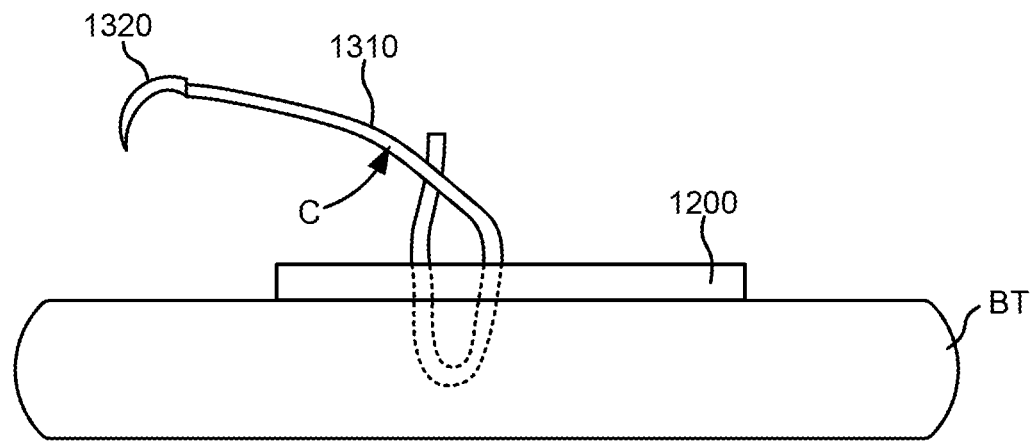

As illustrated in FIG. 17, the energy delivery device 1400 may be removed once the energy has been delivered and the portions of the filament have been fused or coupled together. The filament 1310 may then be cut, for example at location C. The remainder of the filament 1310 (the portion that remains attached to the needle 1320) may be used to repeat the above process to couple another portion of the implant 1200 to the bodily tissue BT. In some embodiments, the filament 1310 may be used to couple the implant 1200 to three, five, ten or more locations or portions of the bodily tissue BT.

Figure 18:
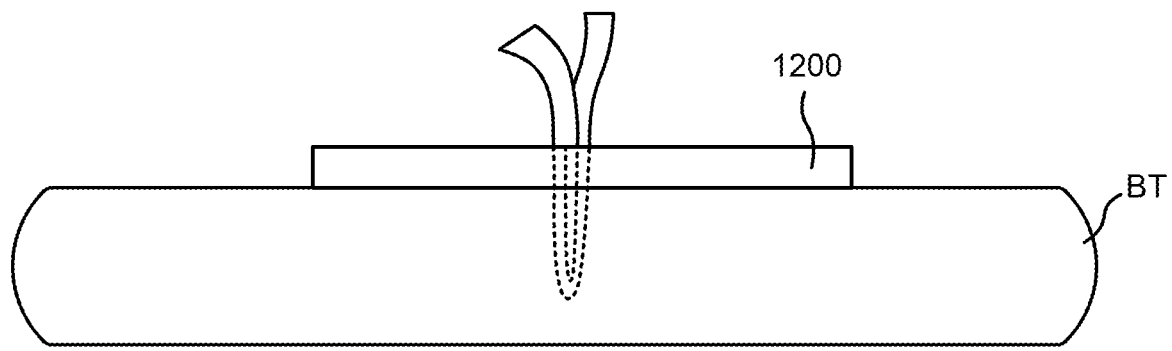

As illustrated in FIG. 18, the fused filament 1310 forms a complete loop through the implant 1200 and the bodily tissue BT. Accordingly, the implant 1200 is coupled to the bodily tissue BT.

Figure 19:
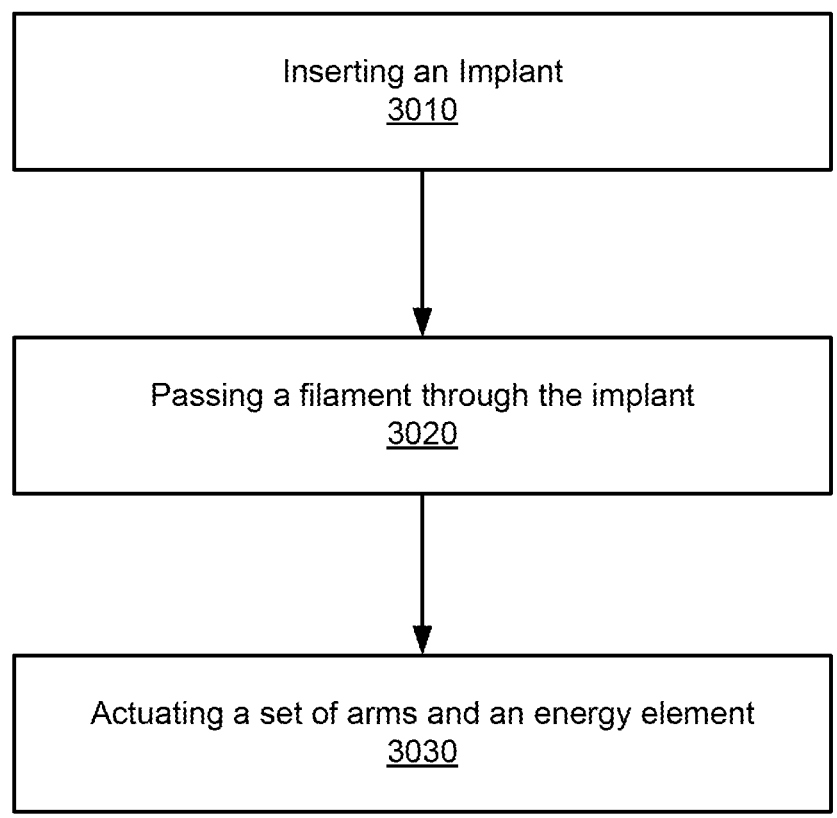
FIG. 19 is a flow chart illustrating a method according to an embodiment of the invention.

FIG. 19 is a flow chart illustrating a method 3000 according to an embodiment of the invention. At 3010, an implant is inserted into the body of the patient such that the implant is disposed adjacent bodily tissue. At 3020 a filament is passed through the implant and through a portion of the bodily tissue. At 3030 an actuation member of an energy delivery device is actuated to move a first arm of the energy delivery device with respect to a second arm of the energy delivery device and deliver energy a first portion of the filament to fuse the first portion of the filament to a second portion of the filament Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this invention. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the disclosure.

What is claimed is:

1. A medical device, comprising:
a filament, at least a portion of the filament having a coating, the coating being configured to stick a first portion of the filament to a second portion of the filament, the filament being coupled to a curved needle; and
an energy delivery device having an elongate member, the elongate member having a first end portion and a second end portion defining a longitudinal axis, a first arm extending from the elongate member and a second arm extending from the elongate member, the first arm being configured to move with respect to the second arm, the energy delivery device including an electrical circuit, the electrical circuit includes an energy element and an energy source, the energy source being disposed in the elongate member, the energy element being configured to deliver energy to a portion of the filament when the filament is disposed between the first arm and the second arm, the filament being configured to extend through at least a portion of an implant, the energy delivery device including a trigger member, the trigger member being configured to move the first arm with respect to the second arm in response to the trigger member being actuated, the energy element being operatively coupled to the trigger member,
the electrical circuit includes a first electrical contact and a second electrical contact, the first electrical contact and the second electrical contact disposed along the longitudinal axis, the first electrical contact being configured to contact the second electrical contact such that energy is delivered to a portion of the filament disposed between the first arm and the second arm in response to the trigger member being actuated.

2. The medical device of claim 1, wherein the energy delivery device is configured to deliver heat energy to the portion of the filament.

3. The medical device of claim 1, wherein the filament is a suture.

4. The medical device of claim 1, wherein the trigger member is configured to simultaneously move the first arm with respect to the second arm and activate the energy element in response to the trigger member being actuated.

5. The medical device of claim 1, wherein the energy delivery device includes a handle portion, the handle portion extending from the elongate member.

6. The medical device of claim 1, wherein the energy delivery device includes a handle portion, the handle portion extending from the elongate member, the handle portion having a portion that extends along an axis that is disposed at an angle with respect to the longitudinal axis of the elongate member.

7. The medical device of claim 1, wherein the first arm is pivotally coupled to the elongate member.

8. The medical device of claim 1, wherein the first arm is pivotally coupled to the elongate member, the second arm is pivotally coupled to the elongate member.

9. The medical device of claim 1, wherein the energy delivery device includes a spring configured to bias the trigger member, the spring extending along an axis parallel to the longitudinal axis of the energy delivery device.

10. A kit, comprising:
an implant configured to be placed within a body of a patient;
a filament having a first end portion and a second end portion, the first end portion of the filament being coupled to a curved needle, the needle being configured to guide the filament through bodily tissue of the patient and the implant, at least a portion of the filament having a coating, the coating being configured to stick a first portion of the filament to a second portion of the filament; and an energy delivery device including an elongate member, a first arm extending from the elongate member and a second arm extending from the elongate member, the first arm being configured to move with respect to the second arm, the energy delivery device including an electrical circuit, the electrical circuit includes an energy element, the energy element being configured to deliver energy to a portion of the filament when the filament is disposed between the first arm and the second arm, the energy delivery device including a trigger member, the trigger member being operatively coupled to the first arm and to the energy element, the trigger member being configured to move the first arm with respect to the second arm and activate the energy element in response to the trigger member being actuated.

11. The kit of claim 10, wherein the energy delivery device is configured to deliver heat energy to the portion of the filament.

12. The kit of claim 10, wherein the filament is a suture.

13. The kit of claim 10, wherein the trigger member is configured to simultaneously move the first arm with respect to the second arm and activate the energy element in response to the trigger member being actuated.

14. The kit of claim 10, wherein the energy delivery device includes a handle portion, the handle portion extending from the elongate member.

15. The kit of claim 10, wherein the energy delivery device includes a handle portion, the handle portion extending from the elongate member, the handle portion having a portion that extends along an axis that is disposed at an angle with respect to a longitudinal axis of the elongate member.

16. The kit of claim 10, wherein a first portion of the filament is configured to extend through a second portion of the filament.

17. The kit of claim 10, wherein a first portion of the filament is coupled to a second portion of the filament to attach the implant to the bodily tissue.

18. The kit of claim 10, wherein the energy delivery device is configured to deliver energy to a third portion of the filament and a fourth portion of the filament to form a loop.

19. The kit of claim 10, wherein the filament is formed of a material that is configured to couple a third portion of the filament to a fourth portion of the filament when energy is applied.

20. The kit of claim 10, wherein the energy delivery device includes a spring configured to bias the trigger member, the spring extending along an axis parallel to a longitudinal axis of the energy delivery device.

* * * * *